(12) United States Patent
Wyrwa et al.

(10) Patent No.: US 7,388,003 B2
(45) Date of Patent: Jun. 17, 2008

(54) $\Delta^{15}$-D-HOMOSTEROIDS WITH ANDROGENIC ACTION

(75) Inventors: Ralf Wyrwa, Rothenstein (DE); Sven Ring, Jena (DE); Guenter Kaufmann, Jena (DE); Walter Elger, Berlin (DE); Birgitt Schneider, Jena (DE)

(73) Assignee: Bayer Schering Pharma AG, Berlin (DE)

( * ) Notice: Subject to any disclaimer, the term of this patent is extended or adjusted under 35 U.S.C. 154(b) by 602 days.

(21) Appl. No.: 10/923,080

(22) Filed: Aug. 23, 2004

(65) Prior Publication Data
US 2005/0131076 A1 Jun. 16, 2005

Related U.S. Application Data

(60) Provisional application No. 60/496,669, filed on Aug. 21, 2003.

(30) Foreign Application Priority Data
Aug. 21, 2003 (DE) ................. 103 39 532

(51) Int. Cl.
*A61K 31/56* (2006.01)
*C07J 1/00* (2006.01)
(52) U.S. Cl. ................. 514/178; 552/502; 514/841
(58) Field of Classification Search ............... 549/384; 552/502; 568/823; 514/178
See application file for complete search history.

(56) References Cited

U.S. PATENT DOCUMENTS 4,057,561 A 11/1977 Fürst et al.

FOREIGN PATENT DOCUMENTS

| GB | 1054262 | 1/1967 |
| GB | 1564144 | 4/1980 |
| GB | 1569221 | 6/1980 |
| WO | WO 2004/032897 A2 | 4/2004 |

OTHER PUBLICATIONS

Avery et al., "Synthesis and testing of 17aβ-hydroxy-7α-methyl-D-homoestra-4, 16-dien-3-one: a highly potent orally active androgen", Steroids, 1990, vol. 55, February, pp. 59-64.
Wölfling et al., "Synthesis of novel halogen-containing D-homoestrone and 13α-D-homoestrone derivatives by Lewis acid-induced intramolecular Prins reaction", Tetrahedron 58 (2002) 6851-6861.
International Search Report for Application No. PCT/EP2004/009468 dated Dec. 17, 2004.

*Primary Examiner*—Barbara P. Badio
(74) *Attorney, Agent, or Firm*—Millen, White, Zelano, Branigan, P.C.

(57) ABSTRACT

The invention relates to $\Delta^{15}$-D-homosteroids of general formula (I)

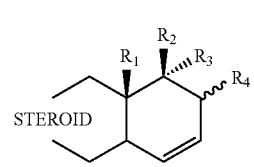

process for their production and pharmaceutical compositions that contain these compounds.

The compounds of general formula I according to the invention have androgenic activity.

21 Claims, No Drawings

$\Delta^{15}$-D-HOMOSTEROIDS WITH ANDROGENIC ACTION

This application claims priority of Provisional Application No. 60/496,669, filed Aug. 21, 2003.

The invention relates to $\Delta^{15}$-D-homosteroids of general formula I

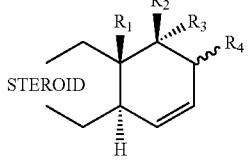
(I)

a process for their production, pharmaceutical compositions that contain these compounds as well as their use for the production of pharmaceutical agents with androgenic action.

$\Delta^{15}$-D-Homosteroids of the estrane or androstane series are not known to date. $\Delta^{16}$-D-Homosteroids, however, which have androgenic as well as antigonadotropic activity, are known from U.S. Pat. No. 4,155,918 and Avery et al., Steroids, 1990, Vol. 55, pp. 59-64).

The object of this invention is to provide other androgenically active compounds as well as a technically simple and effective process for their production.

This object is achieved by $\Delta^{15}$-D-homosteroids of the general formula

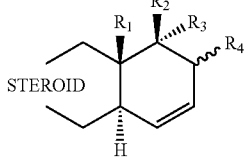
(I)

in which $R^1$ stands for a $C_{1-4}$-alkyl group, and $R^2$ stands for a hydroxy group, a group $OC(O)-R^{20}$, $OC(O)NH-R^{20}$ or $OR^{20}$, whereby $R^{20}$ means a $C_{1-12}$-alkyl group, a $C_{3-8}$-cycloalkyl group, an aryl group or an aryl-$C_{1-4}$- alkyl group, which optionally is substituted, and $R^3$ stands for a hydrogen atom or a $C_{1-6}$-alkyl-, vinyl-, ethinyl- or $C_nF_{2n+1}$ group, with n=1, 2, 3, and $R^4$ stands for a hydrogen atom, or $R^2$ stands for a hydrogen atom or a $C_{1-6}$-alkyl-, vinyl-, ethinyl- or $C_nF_{2n+1}$ group, with n–1, 2, 3, $R^3$ stands for a hydroxy group, a group $OC(O)-R^{20}$, $OC(O)NH-R^{20}$ or $OR^{20}$, whereby $R^{20}$ means a $C_{1-12}$-alkyl group, a $C_{3-8}$-cycloalkyl group, an aryl group or an aryl-$C_{1-4}$- alkyl group, which optionally is substituted, and $R^4$ stands for a hydrogen atom, or $R^2$ and $R^3$ together stand for an oxygen atom, and $R^4$ stands for a hydrogen atom, or $R^2$ stands for a hydroxy group, a group $OC(O)-R^{20}$, $OC(O)NH-R^{20}$ or $OR^{20}$, whereby $R^{20}$ means a $C_{1-12}$-alkyl group, a $C_{3-8}$-cycloalkyl group, an aryl group or an aryl-$C_{1-4}$- alkyl group, which optionally is substituted, and $R^3$ and $R^4$ together form a double bond, and STEROID stands for a steroidal partial ring system of formulas A, B, C, D, E and F:

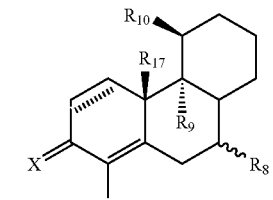
A

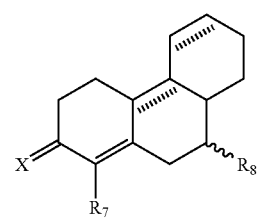
B

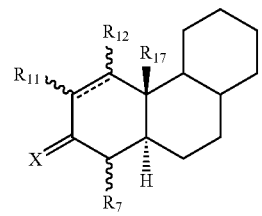
C

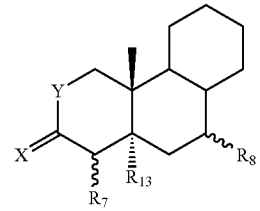
D

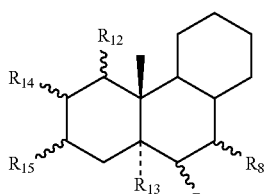
E

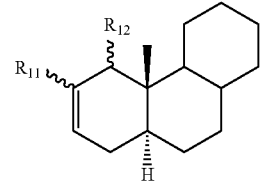
F whereby an additional double bond can be found in A and C in 1,2-position, and one or two additional double bonds can be found in B in 9,10-position and 11,12-position, $R^7$ means a hydrogen atom, a halogen atom, a hydroxy group or a $C_nF_{2n+1}$ group, with n=1, 2, 3, X means an oxygen atom, two hydrogen atoms or a hydroxyimino group, $R^8$ means a hydrogen atom, a methyl or ethyl group, $R^9$ means a hydrogen atom or a halogen atom or together with $R^{10}$ stands for a double bond, $R^{10}$ means a hydrogen atom, a hydroxy group, a methyl or ethyl group or together with $R^9$ stands for a double bond, $R^{11}$ means a hydrogen atom, a $C_{1-4}$-alkyl group, a nitrile group, a hydroxymethylene group or formyl group, $R^{12}$ means a hydrogen atom, a $C_{1-4}$-alkyl group or a nitrile group, $R^{11}$ and $R^{12}$, in addition to the above-mentioned meanings, together mean a methylene bridge, $R^{13}$ means a hydrogen atom or together with $R^7$ means a double bond, $R^{16}$ means a hydrogen atom or together with $R^{13}$ means a double bond, $R^{15}$ means a hydroxyl group, $R^{14}$ and $R^{15}$ stand for a hydrogen atom or together for a double bond, a [2,3c] oxadiazole ring, a [3,2c]isoxazole ring or a [3,2c]pyrazole ring, $R^{17}$ means a hydrogen atom or a methyl group, Y stands for an oxygen or nitrogen atom, whereby the wavy lines at $R^4$, $R^7$, $R^8$, $R^{11}$, $R^{12}$, $R^{13}$, $R^{14}$ and $R^{15}$ mean that these substituents can be in α- or β-position, and their pharmaceutically acceptable salts.

The compounds according to the invention have androgenic activity.

The $C_{1-4}$-alkyl group is a branched or unbranched alkyl radical, which preferably is formed by a methyl-, ethyl-, n-propyl-, i-propyl-, n-butyl-, i-butyl- or tert.-butyl group.

The $C_{1-6}$-alkyl group is a branched or unbranched alkyl radical, which preferably is formed by a methyl-, ethyl-, n-propyl-, i-propyl-, n-butyl-, i-butyl- or tert.-butyl group, n-pentyl, i-pentyl, n-hexyl-, 2-methylpentyl-, 3-methylpentyl-, 2,2-dimethylbutyl-, or 2,3-dimethylbutyl group.

The $C_{1-12}$-alkyl group is a branched or unbranched alkyl radical, which preferably is formed by a methyl-, ethyl-, n-propyl-, i-propyl-, n-butyl-, i-butyl-, tert.-butyl-, n-pentyl-, i-pentyl-, n-hexyl-, 2-methylpentyl-, 3-methylpentyl-, 2,2-dimethylbutyl-, 2,3-dimethylbutyl group, an octyl-, nonyl-, decyl- or undecyl group.

The $C_{3-8}$-cycloalkyl group is preferably a mono- or bicyclic group, such as a cyclopropyl-, cyclobutyl-, cyclopentyl- or cyclohexyl group.

The term aryl group stands for a substituted or unsubstituted aryl radical with preferably 6 to 15 carbon atoms, such as a phenyl group, a substituted phenyl group, such as a halophenyl group or a nitrophenyl group, or a naphthyl group.

The term aryl-$C_{1-4}$-alkyl group is preferably to be an alkyl radical that is substituted with an aryl radical, which together preferably exhibits 7 to 15 carbon atoms, whereby the aryl radical and/or alkyl radical can carry additional substituents, such as preferably a halogen atom, a hydroxy group, a methoxy group or a nitrile group. Especially preferred aryl radicals are a free or aromatically substituted benzyl group, such as a benzyl group or a halobenzyl group.

The term halogen atom stands for a fluorine, chlorine, bromine or iodine atom.

If STEROID stands for a steroidal ring system of partial formula A, $R^7$ preferably means a hydrogen atom, a chlorine atom, a bromine atom, a hydroxy group or a trifluoromethyl group, $R^{10}$ preferably means a hydrogen atom, a hydroxy group or a methyl group, $R^9$ preferably means a hydrogen atom or a fluorine atom, $R^8$ preferably means a hydrogen atom or a methyl group, whereby the methyl group is especially preferred.

If STEROID stands for a steroidal ring system of partial formula B, $R^7$ preferably means a hydrogen atom, a chlorine atom, a bromine atom, or a hydroxy group or a trifluorom- ethyl group, and $R^8$ preferably means a hydrogen atom or a methyl group, whereby the methyl group is especially preferred.

If STEROID stands for a steroidal ring system of partial formula C, $R^7$ preferably means a hydrogen atom, a chlorine atom, a bromine atom or a hydroxy group or a trifluoromethyl group, and $R^{11}$, $R^{12}$ preferably mean a hydrogen atom. Moreover, a double bond in 1,2-position is preferred. For $R^{17}$, H or $CH_3$ is equally preferred.

If STEROID stands for a steroidal ring system of partial formula D, $R^7$ preferably means a hydrogen atom, a chlorine atom, a bromine atom or a hydroxy group, or a trifluoromethyl group, $R^8$ preferably means a hydrogen atom or a methyl group, whereby a methyl group is especially preferred, and $R^{13}$ and $R_7$ together preferably mean a double bond, and Y preferably means an oxygen atom.

If STEROID stands for a steroidal ring system of partial formula E, $R^8$ preferably means a hydrogen atom or a methyl group, whereby a methyl group is especially preferred, $R^{12}$ preferably stands for a hydrogen atom, $R^{13}$ and $R^{16}$ preferably stand for a hydrogen atom or together for a double bond, $R^{15}$ preferably stands in each case for a hydroxy group, or $R^{14}$ and $R^{15}$ together preferably stand for a [3,2c] pyrazole ring.

If STEROID stands for a steroidal ring system of partial formula F, $R^{11}$ preferably means a $C_{1-4}$-alkyl group or nitrile group.

$R^1$ preferably means a methyl group or an ethyl group, whereby the methyl group is especially preferred.

$R^2$ preferably means a hydroxy group, a formyloxy group, acetyloxy group, propionyloxy group, butyryloxy group, [(trans-4-butylcyclohexyl)carbonyl]oxy group, phenylpropionyloxy group, iso-butyryloxy group, heptanyloxy group, undecanyloxy group or phenylaminocarbonyloxy group, whereby the hydroxy group is especially preferred.

$R^3$ preferably means a methyl-, a trifluoromethyl-, an ethyl-, a pentafluoroethyl- or an ethinyl group, whereby the methyl-, ethyl-, trifluoromethyl and pentafluoromethyl group are especially preferred.

$R^4$ preferably means a hydrogen atom.

Especially preferred $\Delta^{15}$-D-homosteroids are indicated below:

1) 17aβ-Hydroxy-D-homo-androstane-4,15-dien-3-one,
2) 17aβ,4-Dihydroxy-D-homo-androstane-4,15-dien-3-one,
3) 17aβ-Hydroxy-4-chloro-D-homo-androstane-4,15-dien-3-one,
4) 17aβ-Hydroxy-4-bromo-D-homo-androstane-4,15-dien-3-one,
5) 17aβ-Hydroxy-4-trifluoromethyl-D-homo-androstane-4,15-dien-3-one,
6) 17aβ, 11β-Dihydroxy-D-homo-androstane-4,15-dien-3-one,
7) 17aβ, 11β-Dihydroxy-D-homo-9α-fluoro-androstane-4,15-dien-3-one,
8) 17aβ-Hydroxy-D-homo-androstane-1,4,15-trien-3-one,
9) 17aβ-Hydroxy-D-homo-4-chloro-androstane-1,4,15-trien-3-one,
10) 17aβ,4-Dihydroxy-D-homo-androstane-1,4,15-trien-3-one,
11) 17aβ-Hydroxy-7α-methyl-D-homo-androstane-1,4,15-trien-3-one,
12) 17aβ-Hydroxy-7α-methyl-4-chloro-D-homo-androstane-1,4,15-trien-3-one,
13) 17aβ-Hydroxy-17α-methyl-androstane-4,15-dien-3-one, 14) 17aβ-Hydroxy-17aα-trifluoromethyl-7α-methyl-androstane-4,15-dien-3-one,
15) 17aβ,4-Dihydroxy-17aα-trifluoromethyl-androstane-4,15-dien-3-one,
16) 17aβ-Hydroxy-17aα-trifluoromethyl-4-chloro-androstane-4,15-dien-3-one,
17) 17aβ-Hydroxy-7α-methyl-D-homo-androstane-4,15-dien-3-one,
18) 17aβ-Hydroxy-17α-pentafluoroethyl-androstane-4,15-dien-3-one,
19) 17aβ-Hydroxy-D-homo-estra-4,15-dien-3-one,
20) 17aβ,4-Dihydroxy-D-homo-estra-4,15-dien-3-one,
21) 17aβ-Hydroxy-4-chloro-D-homo-estra-4,15-dien-3-one,
22) 17aβ-Hydroxy-4-bromo-D-homo-estra-4,15-dien-3-one,
23) 17aβ-Hydroxy-4-trifluoromethyl-D-homo-estra-4,15-dien-3-one,
24) 17aβ-Hydroxy-17aα-methyl-D-homo-estra-4,15-dien-3-one,
25) 17aβ-Hydroxy-17aα-methyl-4-chloro-D-homo-estra-4,15-dien-3-one,
26) 17aα-Hydroxy-17aα-trifluoromethyl-D-homo-estra-4,15-dien-3-one,
27) 17aβ-Hydroxy-17aα-pentafluoroethyl-D-homo-estra-4,15-dien-3-one
28) 17aβ-Hydroxy-7α-methyl-D-homo-estra-4,15-dien-3-one,
29) 17aβ-Hydroxy-7α-methyl-4-chloro-D-homo-estra-4,15-dien-3-one,
30) 17aβ-Hydroxy-D-homo-estra-1,4,15-trien-3-one,
31) 17aβ-Hydroxy-D-homo-4-chloro-estra-1,4,15-trien-3-one,
32) 17aβ,4-Dihydroxy-D-homo-estra-1,4,15-trien-3-one,
33) 17aβ-Hydroxy-7α-methyl-D-homo-estra-1,4,15-trien-3-one,
34) 17aβ-Hydroxy-7α-methyl-4-chloro-D-homo-estra-1,4,15-trien-3-one,
35) 13-Ethyl-17aβ-hydroxy-D-homo-gona-4,15-dien-3-one,
36) 13-Ethyl-17aβ-hydroxy-4-chloro-D-homo-gona-4,15-dien-3-one,
37) 13-Ethyl-17aβ-hydroxy-7α-methyl-D-homo-gona-4,15-dien-3-one,
38) 13-Ethyl-17aβ-hydroxy-17α-methyl-D-homo-gona-4,15-dien-3-one,
39) 13-Ethyl-17aβ-hydroxy-17α-methyl-4-chloro-D-homo-gona-4,15-dien-3-one,
40) 13-Ethyl-17aβ-hydroxy-D-homo-gona-1,4,15-trien-3-one,
41) 13-Ethyl-17aβ-hydroxy-4-chloro-D-homo-gona-1,4,15-trien-3-one,
42) 13-Ethyl-17aβ-hydroxy-7α-methyl-D-homo-gona-1,4,15-trien-3-one,
43) 13-Ethyl-17aβ-hydroxy-7α-methyl-4-chloro-D-homo-gona-1,4,15-trien-3-one,
44) 17aβ-Hydroxy-D-homo-5α-androst-15-en-3-one,
45) 2-Oxa-17aβ-hydroxy-D-homo-5α-androst-15-en-3-one,
46) 17aβ-Hydroxy-D-homo-5α-androstane-1,15-dien-3-one,
47) 2-Hydroxymethylene-17aβ-hydroxy-D-homo-5α-androst-15-en-3-one.

Another subject of the invention is a technically simple and effective process for the production of $\Delta^{15}$-D-homosteroids of general formula (I).

In this respect, compounds of general formula (II) (M. A. Avery et al., Steroids, 1990, 55, 59-64; A. Fürst et al., 1976, U.S. Pat. No. 3,984,476.) are known

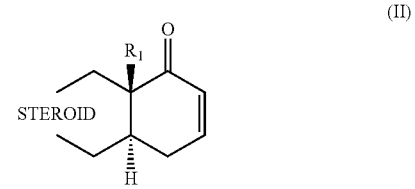

in which $R^1$ and STEROID, which have the meaning indicated above, are reacted in a known way, in the presence of acids, such as, e.g., p-toluenesulfonic acid, with acylating agents, such as, e.g., isopropenyl acetate (Hosoda, H. et al., Chem. Phar. Bull., 23, 1975, 3141-3145), acetic acid anhydride (Rasmusson, G. H., Arth, G. E., Steroids, 22,1973, 107-111) or the like to form the dienol acetates and then reduced with reducing agents, such as, e.g., NaBH$_4$, to the corresponding 17aβ-hydroxy-D-homo-$\Delta^{15}$-steroids.

For the production of the compounds of general formula II with partial structures A to F, known steroid bases can be used.

The following steroid bases can be used, for example:

For steroid base A: androst-4-ene-3,17-dione and dehydroepiandrosterone.

For steroid base B: estrone, 7α-methylestrone.

For steroid base C, D or E: epiandrosterone.

For steroid base F: 5α-androst-2-en-17-one from epiandrosterone (U.S. Pat. No. 3,098,851).

The functional groups that are contained in the partial structures of the starting materials for steroid bases A to F can optionally be protected according to the methods known to one skilled in the art.

Keto groups in the starting materials of partial structures A to F thus can be protected as ketals or thioacetals according to the methods that are known to one skilled in the art. The introduction of substituents $R^7$ to $R^{15}$ in partial structures A to F can be carried out both before and after the incorporation of the D-homo-$\Delta^{15}$-cyclic compound according to methods that are known to one skilled in the art.

For the formation of pharmaceutically compatible salts of the compounds of general formula I according to the invention, i.a., hydrochloric acid, hydrobromic acid, sulfuric acid and phosphoric acid are considered as inorganic acids, and, i.a., acetic acid, propionic acid, maleic acid, fumaric acid, succinic acid, benzoic acid, ascorbic acid, oxalic acid, salicylic acid, tartaric acid, citric acid, lactic acid, malic acid, mandelic acid, cinnamic acid, and methanesulfonic acid are considered as organic acids.

The compounds according to the invention have androgenic activity, as depicted below in Table 1.

TABLE 1

Relative Binding Affinities/RBA to the Androgen Receptor Compared to Testosterone and Methyltrienolone

| Compound | RBA % |
| --- | --- |
| Testosterone | 35 |
| R 1881 (Methyltrienolone) | 100 |
| 17aβ-Hydroxy-D-homo-androstane-4,15-dien-3-one | 12 |
| 17aβ-Hydroxy-D-homo-estra-4,15-dien-3-one | 25 |

17aβ-Hydroxy-7α-methyl-D-homoestra-4,16-dien-3-one is described in Steroids, 1990, 55, 59-64 as androgen with antigonadotropic properties. 17aβ-Hydroxy-7α-methyl-D-homoestra-4,16-dien-3-one, however, shows only a slight receptor binding affinity to the androgen receptor of 2% (reference DHT=100%).

Completely unexpectedly and surprisingly enough, the $\Delta^{15}$-D-homosteroids according to the invention show a significantly higher binding affinity to the androgen receptor. They bind $\Delta^{15}$-D-homo compounds in comparison to 17aβ-hydroxy-7α-methyl-D-homoestra-4,16-dien-3-one (Steroids 1990, 55, 59-64) with >12% (reference DHT=100%) to the androgen receptor. Thus, a mediation of androgenic activity in the $\Delta^{15}$-D-homosteroids according to the invention that is different from the 17aβ-hydroxy-7α-methyl-D-homoestra-4,16-dien-3-one (Steroids, 1990, 55, 59-64) that is known in the literature is suggested.

In the compounds according to the invention, these test results open up many possibilities for birth control in men and women, hormone replacement therapy (HRT) in men and women, or the treatment of hormonally-induced diseases in men and women, such as, for example, endometriosis, breast cancer or hypogonadism.

Subjects of this invention are therefore also pharmaceutical compositions that contain at least one $\Delta^{15}$-D-homosteroid of general formula (I), optionally together with pharmaceutically compatible adjuvants and vehicles, such as also the use of these compounds, i.a., for therapy or for the production of pharmaceutical preparations, i.a., for therapy of the previously mentioned clinical pictures.

These pharmaceutical compositions and pharmaceutical agents can be provided for oral, rectal, vaginal, subcutaneous, percutaneous, intravenous or intramuscular administration. In addition to commonly used vehicles and/or diluents, they contain at least one compound of general formula I.

The pharmaceutical agents of the invention are produced with a suitable dosage in a known way with the commonly used solid or liquid vehicles or diluents and the commonly used pharmaceutical-technical adjuvants corresponding to the desired type of administration. The preferred preparations consist in a form for dispensing that is suitable for oral administration. Such forms for dispensing are, for example, tablets, film tablets, coated tablets, capsules, pills, powders, solutions or suspensions or else depot forms.

Of course, parenteral preparations such as injection solutions are also considered. In addition, for example, suppositories and agents for vaginal application can also be mentioned as preparations.

Corresponding tablets can be obtained by, for example, mixing the active ingredient with known adjuvants, for example inert diluents, such as dextrose, sugar, sorbitol, mannitol, polyvinylpyrrolidone, explosives such as corn starch or alginic acid, binders such as starch or gelatin, lubricants such as magnesium stearate or talc, and/or agents for achieving a depot effect, such as carboxylpolymethylene, carboxylmethyl cellulose, cellulose acetate phthalate or polyvinyl acetate. The tablets can also consist of several layers.

Coated tablets can accordingly be produced by coating cores, which are produced analogously to the tablets, with agents that are commonly used in tablet coatings, for example polyvinylpyrrolidone or shellac, gum arabic, talc, titanium oxide or sugar. In this case, the coated tablet shell can also consist of several layers, whereby the adjuvants that are mentioned above in the tablets can be used.

Solutions or suspensions with the compounds of general formula I according to the invention can contain additional taste-improving agents, such as saccharine, cyclamate or sugar, as well as, e.g., flavoring substances, such as vanilla or orange extract. In addition, they can contain suspending adjuvants, such as sodium carboxy methyl cellulose, or preservatives, such as p-hydroxybenzoates.

Capsules that contain the compounds of general formula I can be produced, for example, by the compound(s) of general formula I being mixed with an inert vehicle, such as lactose or sorbitol, and encapsulated in gelatin capsules.

Suitable suppositories can be produced by, for example, mixing with vehicles that are provided for this purpose, such as neutral fats or polyethylene glycol or derivatives thereof.

The examples below explain this invention without being limited thereto.

EXAMPLE 1

17aβ-Hydroxy-D-homoestra-4,15-dien-3-one

Stage 1

3-Methoxy-17a-acetoxy-D-homoestra-1,3,5(10),15,17-pentaene 4.0 g of 3-methoxy-D-homoestra-1,3,5(10),16-tetraen-17a-one is dissolved in 40 ml of acetic acid anhydride and 40 ml of isopropenyl acetate. After 2.0 g of p-toluenesulfonic acid is added, it is heated for 48 hours to 80° C. Then, it is neutralized with saturated NaHCO$_3$ solution. The substance is extracted with ethyl acetate, the organic phase is washed with saturated NaCl solution, dried on MgSO$_4$, filtered, concentrated by evaporation and chromatographed on silica gel. 3-Methoxy-17a-acetoxy-D-homoestra-1,3,5(10),15,17-pentaene is obtained.

$^1$H-NMR (CDCl$_3$): 0.96 (s, 3H, H-18), 2.20 (s, 3H, OAc), 3.78 (s, 3H, OCH$_3$), 5.65-6.05 (m, 3H, H-15, H-16, H-17)

Stage 2

3-Methoxy-17aβ-hydroxy-D-homoestra-1,3,5(10),15-tetraene 6.5 g of 3-methoxy-D-homo-estra-1,3,5(10),15,17-pentaen-17a-yl-acetate is dissolved in 150 ml of methanol and 75 ml of THF. While being stirred at −20° C., 5.0 g of NaBH$_4$ is added in portions, and it is stirred for 3 hours. Then, it is concentrated by evaporation to ⅕, and 250 ml of water is added. Then, the remaining organic solvent is distilled off. The substance is filtered off, washed with water, dried in a vacuum, and chromatographed on silica gel. 3-Methoxy-17aβ-hydroxy-D-homoestra-1,3,5(10),15-tetraene is obtained.

$^1$H-NMR (CDCl$_3$): 0.81 (s, 3H, H-18), 3.64 (m, 1H, H-17a), 3.77 (s, 3H, OCH$_3$), 5.60-5.80 (m, 2H, H-1S, H-16)

Stage 3

3-Methoxy-17aβ-hydroxy-D-homoestra-1,3,5(10),15-triene 5.0 g of 3-methoxy-17aβ-hydroxy-D-homoestra-2,5(10),15-tetraene, dissolved in 35 ml of THF and 15 ml of 1-methoxy-2-propanol, is added in drops at −70° C. inca solution that consists of 100 ml of liquid ammonia, 10 ml of THF, and about 0.3 g of sodium. After bleaching, the addition is interrupted, and sodium is added again. After 2.5 g of Na is added, the reaction is completed. 2.5 ml of isopropanol and 8 g of solid NH$_4$Cl are added. While being heated slightly, the ammonia is evaporated. After 250 ml of cold water is added, the steroid is filtered off, washed neutral with water and dried in a vacuum. 3-Methoxy-17aβ-hydroxy-D-homoestra-1,3,5(10),15-triene is obtained.

Stage 4

17aβ-Hydroxy-D-homoestra-4,15-dien-3-one 4.6 g of 3-methoxy-17aβ-hydroxy-D-homoestra-1,3,5 (10),15-triene is dissolved in 150 ml of acetone. While being stirred at room temperature, 8 ml of 5% aqueous hydrochloric acid is added in drops. After 1 hour, 50 ml of saturated NaHCO₇ solution and 150 ml of water are added. Then, the acetone is distilled off to a very large extent. The substance is filtered off, washed with water, dried in a vacuum and chromatographed on silica gel. 17aβ-Hydroxy-D-homoestra-4,15-dien-3-one is obtained.

$^1$H-NMR (CDCl$_3$): 0.84 (s, 3H, H-18), 3.57 (m, 1H, H-17a), 5.57-5.72 (m, 2H, H-15, H-16), 5.84 (s, 1H, H-4)

EXAMPLE 2

17aβ-Hydroxy-D-homoandrost-4,15-dien-3-one

Stage 1

3β-Acetoxy-17a-acetoxy-D-homoandrostane-5,15,17-triene 6.0 g of 3β-acetoxy-D-homoandrostane-5,16-dien-17a-one is dissolved in 70 ml of acetic acid anhydride and 70 ml of isopropenyl acetate. After 4.0 g of p-toluenesulfonic acid is added, it is heated for 48 hours to 80° C. Then, it is neutralized with saturated NaHCO$_3$ solution. The substance is extracted with ethyl acetate, the organic phase is washed with saturated NaCl solution, dried on MgSO$_4$, filtered, concentrated by evaporation and chromatographed on silica gel. 3β-Acetoxy-17a-acetoxy-D-homoandrostane-5,15,17-triene is obtained.

$^1$H-NMR (CDCl$_3$): 0.95 (s, 3H, H-18), 1.02 (s, 3H, H-19), 2.04 (s, 3H, OAc), 2.18 (s, 3H, OAc), 4.60 (m, 1H, H-3), 5.41 (m, 1H, H-6), 5.60-5.98 (m, 3H, H-15, H-16, H-17)

Stage 2

3β-Acetoxy-17aβ-hydroxy-D-homoandrostane-5,15-diene 5.0 g of 3β,17a-diacetoxy-D-homoandrosta-4,15,17-triene is dissolved in 200 ml of methanol and 150 ml of THF. While being stirred at −20° C., 5.0 g of NaBH$_4$ is added in portions, and it is stirred for 2 hours. Then, 100 ml of saturated NH$_4$Cl solution is added. Then, the organic solvent is distilled off. After 250 ml of water is added, the substance is filtered off, washed with water, dried in a vacuum and chromatographed on silica gel. 3β-Acetoxy-17aβ-hydroxy-D-homoandrostane-5,15-diene is obtained.

Stage 3

3β-Acetoxy-D-homoandrostane-5,15-diene-17aβ-tetrahydropyranyl ether 4.25 g of 3β-acetoxy-17aβ-hydroxy-D-homoandrostane-5,15-diene is dissolved in 75 ml of methylene chloride. While being stirred at room temperature, 7.5 ml of dihydropyran and 500 mg of pyridinium tosylate are added in succession. After 3 hours, it is washed with 10% NaHCO$_3$ solution and saturated NaCl solution, dried on MgSO$_4$, filtered and concentrated by evaporation. 3β-Acetoxy-D-homoandrostane-5,15-diene-17aβ-tetrahydropyranyl ether is obtained.

Stage 4

3β-Hydroxy-D-homoandrostane-5,15-diene-17aβ-tetrahydropyranyl Ether 5.2 g of 3β-acetoxy-D-homoandrostane-5,15-diene-17aβ-tetrahydropyranyl ether is dissolved in 175 ml of methanol and 125 ml of THF. While being stirred vigorously, 7.5 g of K$_2$CO$_3$ and 2.5 ml of water are added. After 3.5 hours, it is concentrated by evaporation to approximately ⅙. Then, 250 ml of water is added, the substance is filtered off, washed with water and dried in a vacuum. 3β-Hydroxy-D-homoandrostane-5,15-diene-17aβ-tetrahydropyranyl ether is obtained.

Stage 5

3-Keto-D-homoandrostane-4,15-diene-17aβ-tetrahydropyranyl Ether 4.5 g of 3β-hydroxy-D-homoandrostane-5,15-diene-17aβ-tetrahydropyranyl ether is dissolved under argon in 125 ml of toluene. After 1.6 g of Al(O-iPr)$_3$ is added, it is heated for 2.5 hours to 110° C. At room temperature, it is washed two times with 250 ml each of 1 M K—Na-tartrate solution. The aqueous phases are subsequently re-extracted with ethyl acetate. The combined organic phases are washed with saturated NaCl solution, dried on MgSO$_4$, filtered, and concentrated by evaporation in a vacuum. 3-Keto-D-homoandrostane-4,15-diene-17aβ-tetrahydropyranyl ether is obtained.

Stage 6

17aα-Hydroxy-D-homoandrostane-4,15-dien-3-one 14 g of crude product of 3-keto-D-homoandrostane-4,15-diene-17aβ-tetrahydropyranyl ether is dissolved in 100 ml of acetone. At room temperature, 10 ml of 10% hydrochloric acid is added in drops. After 2 hours, 50 ml of saturated NaHCO$_3$ solution is added. The reaction mixture is concentrated by evaporation to approximately ⅓. Then, 150 ml of water is added, and the precipitated substance is filtered off, washed with water, dried in a vacuum and chromatographed on silica gel. 17aβ-Hydroxy-D-homoandrostane-4,15-dien-3-one is obtained.

$^1$H-NMR (CDCl$_3$): 0.82 (s, 3H, H-18), 1.20 (s, 3H, H-19), 3.54 (m, 1H, H-17a), 5.55-5.67 (m, 2H, H-15, H16), 5.74 (s, 1H, H-4)

EXAMPLE 3

17aβ-Hydroxy-4-chloro-D-homoandrostane-4,15-dien-3-one

Stage 1

17aβ-Hydroxy-4ξ,5ξ-epoxy-D-homoandrost-15-en-3-one 2.0 g of 17aβ-hydroxy-D-homoandrosta-4,15-dien-3-one is dissolved in 80 ml of methanol and mixed at 0° C. with 20 ml of hydrogen peroxide solution (35%). While being stirred, 4 ml of 10% sodium hydroxide solution is added, and it is stirred for 3 hours. The reaction solution is concentrated by evaporation to 50 ml, then mixed with 50 ml of dichloromethane and 25 ml of water, and the organic phase is separated. It is washed with semi-concentrated thiosulfate solution, dried and evaporated to the dry state. The residue that is obtained consists of a mixture of 4α,5α- or 4β,5β-epoxides and is used without further purification in the next stage.

Stage 2

17aβ-Hydroxy-4-chloro-D-homoandrostane-4,15-dien-3-one 1.93 g of epoxide mixture (stage 1) is dissolved in 300 ml of acetone and mixed at 0° C. with 17 ml of concentrated hydrochloric acid. After 2 hours, it is neutralized with soda solution, and the acetone is drawn off. The residue is extracted out with dichloromethane. The organic extracts are dried and concentrated by evaporation. After crystallization from ethyl acetate, 17aβ-hydroxy-4-chloro-D-homoandrostane-4,15-dien-3-one is obtained.

$^1$H-NMR (COCL$_3$): 0.82 (s, 3H, H-18), 1.25 (s, 3H, H-19), 3.57 (m, 1H, H-17a), 5.64 (m, 2H, H-15, H-16)

EXAMPLE 4

17aβ-Hydroxy-7α-methyl-D-homoandrostane-4,15-dien-3-one

Stage 1

17aβ-Hydroxy-D-homoandrostane-4,6,15-trien-3-one 2.5 g of 17aβ-hydroxy-D-homoandrostane-4,15-dien-3-one is refluxed with 2.5 g of chloranil in 80 ml of tert.-butanol for 30 minutes. It is allowed to cool and evaporated to the dry state. The residue is chromatographed on silica gel.

Stage 2

17aβ-Hydroxy-7α-methyl-D-homoandrostane-4,15-dien-3-one 100 ml of THF is added to a solution of methylmagnesium iodide (prepared from 1.75 g of magnesium and 5 ml of methyl iodide in 25 ml of diethyl ether), it is cooled to −5° C., and 0.35 g of copper(I)chloride is added. It is cooled to −20° C., and then a solution of 1.3 g of 17aβ-hydroxy-D-homoandrostane-4,6,15-trien-3-one in 20 ml of THF is added in drops. After 2 hours, it is poured into ice water/2N sulfuric acid, and it is extracted with 3×30 ml of methylene chloride. The organic extract is dried and concentrated by evaporation. The residue is chromatographed on silica gel. For further purification, it is recrystallized from ethyl acetate.

$^1$H-NMR (CDCl$_3$): 0.77 (d, J=7 Hz, 3H, H-7Me), 0.83 (s, 3H, H-18), 1.20 (s, 3H, H-19), 3.57 (m, 1H, H-17a), 5.63 (m, 2H, H-15, H-16), 5.74 (s, 1H, H-4)

EXAMPLE 5

17aβ-Hydroxy-4-chloro-D-homoestra-4,15-dien-3-one

Stage 1

17aβ-Hydroxy-4ξ,5ξ-epoxy-D-homoestr-15-en-3-one

The production is carried out analogously to 17aβ-hydroxy-4ξ,5ξ-epoxy-D-homoandrost-15-en-3-one. The residue that is obtained consists of a mixture of 4α,5α- or 4β,5β-epoxides and is used without further purification in the next stage.

Stage 2

17aβ-Hydroxy-4-chloro-D-homoestra-4,15-dien-3-one

The production is carried out from 17aβ-hydroxy-4-chloro-D-homoandrostane-4,15-dien-3-one analogously to 17β-hydroxy-17α-trifluoromethyl-4-chloro-androst-4-en-3-one.

$^1$H-NMR(CDCl$_3$): 0.84 (s, 3H, H-18), 3.57 (m, 1H, H-17a), 5.58-5.70 (m, 2H, H-15, H-16)

EXAMPLE 6

17aβ-Hydroxy-D-homo-5α-androst-15-en-3-one

Stage 1

3β-17a-Diacetoxy-D-homo-5α-androstane-15,17-diene 14.5 g of 3β-acetoxy-D-homoandrostane-5,16-dien-17a-one is dissolved in 200 ml of acetic acid anhydride and 200 ml of isopropenyl acetate. After 5.0 g of p-toluenesulfonic acid is added, it is refluxed for 16 hours. The substance is extracted with ethyl acetate, the organic phase is washed with saturated NaCl solution, and dried on MgSO$_4$, filtered, concentrated by evaporation and chromatographed on silica gel. 3β-Acetoxy-17a-acetoxy-D-homo-5a-androstane-15,17-diene is obtained.

$^1$H-NMR (CDCl$_3$): 0.82 (s, 3H, H-18), 0.92 (s, 3H, H-19), 2.02 (s, 3H, Oac), 2.17 (s, 3H, =Ac), 4.68 (m, 1H, H-3), 5.60-5.92 (m, 3H, H-15, H-16, H-17)

Stage 2

3β-Acetoxy-17aβ-hydroxy-D-homo-5α-androstan-15-ene 8.5 g of 3β,17a-diacetoxy-D-homo-5α-androstane-15,17-diene is dissolved in 360 ml of methanol and 270 ml of THF. While being stirred at −20° C., 6.75 g of NaBH$_4$ is added in portions, and it is stirred for 2 hours at 0° C. Then, 200 ml of saturated NH$_4$Cl solution is added, and it is stirred for 2 hours at 0° C. Then, 200 ml of saturated NH$_4$Cl solution is added. Then, the organic solvent is distilled off. After 100 ml of water is added, the substance is filtered off, washed with water, dried in a vacuum and chromatographed on silica gel. 3β-Acetoxy-17αβ-hydroxy-D-homo-5α-androst-15-ene is obtained.

$^1$H-NMR (CDCl$_3$): 0.76 (s, 3H, H-18), 0.83 (s, 3H, H-19), 2.02 (s, 3H, OAc), 3.53 (m, 1H, 17 a-H), 4.69 (m, 1H, H-3), 5.60-5.65 (m, 2H, H-15, H-16)

Stage 3

3β-Acetoxy-D-homo-5α-androst-15-ene-17aβ-tetrahydropyranyl Ether 7.60 g of 3β-acetoxy-17-ab-hydroxy-D-homo-5a-androst-15-ene is dissolved in 135 ml of methylene chloride. While being stirred at room temperature, 13.5 ml of dihydropyran and 900 mg of pyridinium tosylate are added in succession. After 3 hours, it is washed with 10% NaHCO$_3$ solution and saturated NaCl solution, dried on MgSO$_4$, filtered and concentrated by evaporation. 3β-Acetoxy-D-homoandrostane-5,15-diene-17aβ-tetrahydropyranyl ether is obtained.

Stage 4

3β-Hydroxy-D-homo-5α-androst-15-ene-17aβ-tetrahydropyranyl Ether 12.0 g of 3β-acetoxy-D-homo-5α-androst-15-ene-17aβ-tetrahydropyranyl ether is dissolved in 150 ml of methanol and 100 ml of THF. While being stirred vigorously, 15 g of K$_2$CO$_3$ and 5 ml of water are added. After 3.5 hours, it is concentrated by evaporation to approximately ⅙, washed with water and dried in a vacuum. 3β-Hydroxy-D-homo-5α-androst-15-ene-17aβ-tetrahydropyranyl ether is obtained.

Stage 5

3-Keto-D-homo-5α-androst-15-ene-17aβ-tetrahydropnranyl Ether 9.2 g of 3β-hydroxy-D-homo-5α-androst-15-ene-17-aβ-tetrahydropyranyl ether is dissolved under argon in 200 ml of toluene. After 3.0 g of Al(O-iPr)$_3$ is added, it is heated for 1.5 hours to 110° C. At room temperature, it is washed 2× with 250 ml each of 1 M K—Na-tartrate solution. The aqueous phases are subsequently re-extracted with ethyl acetate. The combined organic phases are washed with saturated NaCl solution, dried on MgSO4, filtered and concentrated by evaporation in a vacuum. 3-Keto-D-homo-5α-androst-15-ene-17aβ-tetrahydropyranyl ether is obtained.

Stage 6

17aβ-Hydroxy-D-homo-5α-androst-15-en-3-one 15.7 g of crude product of 3-keto-D-homo-5α-androst-15-ene-17aβ-tetrahydropyranyl ether is dissolved in 100 ml of acetone. At room temperature, 10 ml of 10% hydrochloric acid is added in drops. After 2 hours, 50 ml of saturated NaHCO$_3$ solution is added. The reaction mixture is concentrated by evaporation to approximately ⅓. Then, 150 ml of water is added, and the precipitated substance is filtered off, washed with water, dried in a vacuum and chromatographed on silica gel. 17aβ-Hydroxy-D-homo-5α-androst-15-en-3-one is obtained.

$^1$H-NMR (CDCl$_3$): 0.76 (s, 3H, H-18), 1.02 (s, 3H, H-19), 3.53 (m, 1H, H-17a), 5.57-5.65 (m, 2H, H-15, H16)

EXAMPLE 7

2-Hydroxymethylene-17aβ-hydroxy-D-homo-5α-androst-15-en-3-one 2.1 g of 17aβ-hydroxy-D-homo-5α-androst-15-en-3-one is introduced under a cover gas into 80 ml of toluene. Then, 2.1 g of NaOH and 4.0 ml of ethyl formate are added. After 1 hour, 2 ml of methanol is added in drops. Then, 50 ml of water is added, and it is acidified with 5N HCl. It is extracted with ethyl acetate. The organic phase is washed with NaHCO$_3$ solution, dried on MgSO$_4$, filtered and concentrated by evaporation. It is chromatographed on silica gel. 2-Hydroxymethylene-17-aβ-hydroxy-D-homo-5α-androst-15-en-3-one is obtained.

$^1$H-NMR (CDCl$_3$): 0.78 (s, 3H, H-18), 0.79 (s, 3H, H-19), 3.55 (m, 1H, H-17a), 5.55-5.67 (m, 2H, H-15, H16), 8.64 (s, 1H, =CH(OH)), 14.37 (s, 1H, =CH(OH))

The invention claimed is:
1. Δ$^{15}$-D-Homosteroids of formula I,

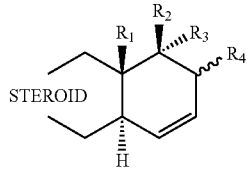

(I)

wherein
R$^1$ stands for a C$_{1-4}$-alkyl group, and
R$^2$ stands for a hydroxy group, a formyloxy group, a group OC(O)—R$^{20}$, OC(O)NH—R$^{20}$, or OR$^{20}$, whereby
R$^{20}$ means a C$_{1-12}$-alkyl group, a C$_{3-8}$-cycloalkyl group, an aryl group or an aryl-C$_{1-4}$-alkyl group, which optionally is substituted, and
R$^3$ stands for a hydrogen atom or a C$_{1-6}$-alkyl-, vinyl-, ethinyl- or C$_n$F$_{2n+1}$ group, with n=1, 2, 3, and
R$^4$ stands for a hydrogen atom, or R$^2$ stands for a hydrogen atom or a C$_{1-6}$-alkyl-, vinyl-, ethinyl- or C$_n$F$_{2n+1}$ group, with n=1, 2, 3,
R$^3$ stands for a hydroxy group, a group OC(O)—R$^{20}$, OC(O)NH—R$^{20}$ or OR$^{20}$, whereby R$^{20}$ means a C$_{1-12}$-alkyl group, a C$_{3-8}$-cycloalkyl group, an aryl group or an aryl-C$_{1-4}$-alkyl group, which optionally is substituted, and
R$^4$ stands for a hydrogen atom, or
R$^2$ and R$^3$ together stand for an oxygen atom, and
R$^4$ stands for a hydrogen atom, or
R$^2$ stands for a hydroxy group, a formyloxy group, a group OC(O)—R$^{20}$, OC(O)NH—R$^{20}$ or OR$^{20}$,
whereby R$^{20}$ means a C$_{1-12}$-alkyl group, a C$_{3-8}$-cycloalkyl group, an aryl group or an aryl-C$_{1-4}$-alkyl group, which optionally is substituted, and
R$^3$ and R$^4$ together form a double bond, and
STEROID stands for a steroidal ABC partial ring system of formulas A, B, C, D, E and F:

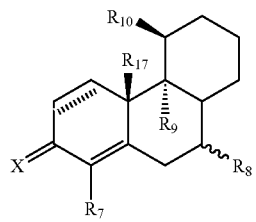

A

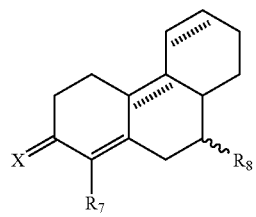

B

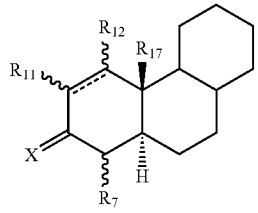

C

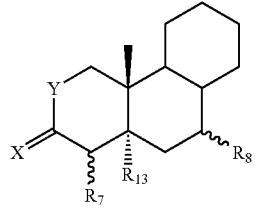

D

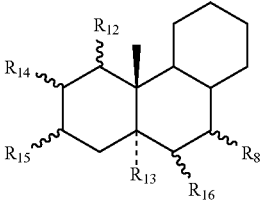

E

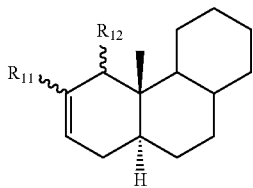

whereby an additional double bond can be found in A and C in 1,2-position, and one or two additional double bonds can be found in B in 9,10-position and 11,12-position, $R^7$ means a hydrogen atom, a halogen atom, a hydroxy group or a $C_nF_{2n+1}$ group, with n=1, 2, 3, X means an oxygen atom, two hydrogen atoms or a hydroxyimino group, $R^8$ means a hydrogen atom, a methyl or ethyl group, $R^9$ means a hydrogen atom or a halogen atom or together with $R^{10}$ stands for a double bond, $R^{10}$ means a hydrogen atom, a hydroxy group, a methyl or ethyl group or together with $R^9$ stands for a double bond, $R^{11}$ means a hydrogen atom, a $C_{1-4}$-alkyl group, a nitrile group, a hydroxymethylene group or formyl group, $R^{12}$ means a hydrogen atom, a $C_{1-4}$-alkyl group or a nitrile group, $R^{11}$ and $R^{12}$, in addition to the above-mentioned meanings, together mean a methylene bridge, $R^{13}$ means a hydrogen atom or together with $R^7$ means a double bond, $R^{16}$ means a hydrogen atom or together with $R^{13}$ means a double bond, $R^{15}$ means a hydroxyl group, $R^{14}$ and $R^{15}$ stand for a hydrogen atom or together for a double bond, a [2,3c] oxadiazole ring, a [3,2c]isoxazole ring or a [3,2c] pyrazole ring, and $R^{17}$ means a hydrogen atom or a methyl group, Y stands for an oxygen or nitrogen atom, whereby the wavy lines at $R^4$, $R^7$, $R^8$, $R^{11}$, $R^{12}$, $R^{13}$, $R^{14}$ and $R^{15}$ mean that these substituents can be in α- or β-position, with the proviso that 17aβ-Hydroxy-D-homo-androstane-4,15-dien-3-one is excluded.

2. A compound according to claim 1, wherein
$R^1$ stands for a methyl group or an ethyl group.

3. A compound according to claim 1, wherein
$R^2$ means a hydroxy group, a formyloxy group, acetyloxy group, propionyloxy group, butyryloxy group, [(trans-4-butylcyclohexyl)carbonyl]oxy group, phenylpropionyloxy group, iso-butyryloxy group, heptanyloxy group, udecanyloxy group or phenylaminocarbonyloxy group.

4. A compound according to claim 1, wherein
$R^3$ means a methyl-, a trifluoromethyl-, an ethyl-, a pentafluoroethyl- or an ethinyl group.

5. A compound according to one of claim 1, wherein
$R^4$ means a hydrogen atom.

6. A compound according to claim 1, wherein
STEROID stands for a steroidal ring system of partial formula A, whereby $R^7$ represents a hydrogen atom, a chlorine atom, a bromine atom, a hydroxy group or a trifluoromethyl group, $R^{10}$ represents a hydrogen atom, a hydroxy group or a and $R^9$ represents a hydrogen atom or a fluorine atom, and $R^8$ represents a hydrogen atom or a methyl group.

7. A compound according to claim 1, wherein
STEROID stands for a steroidal ring system of partial formula B, whereby $R^7$ represents a hydrogen atom, a chlorine atom, a bromine atom, a hydroxy group or a trifluoromethyl group, and $R^8$ represents a hydrogen atom or a methyl group.

8. A compound according to claim 1, wherein
STEROID stands for a steroidal ring system of partial formula C, whereby $R^7$ represents a hydrogen atom, a chlorine atom, a bromine atom or a hydroxy group, or a trifluoromethyl group, and $R^{11}$ as well as $R^{12}$ in each case represent a hydrogen atom, and wherein a double bond is in 1,2-position.

9. A compound according to claim 1, wherein
STEROID stands for a steroidal ring system of partial formula D, whereby $R^7$ represents a hydrogen atom, a chlorine atom, a bromine atom, a hydroxy group or a trifluoromethyl group, and $R^8$ represents a hydrogen atom or a methyl group, and $R^{13}$ and $R^7$ together represent a double bond, and Y represents an oxygen atom.

10. A compound according to claim 1, wherein
STEROID stands for a steroidal ring system of partial formula E, whereby $R^8$ represents a hydrogen atom or a methyl group, $R^{12}$ represents a hydrogen atom, $R^{13}$ and $R^{16}$ in each case represent a hydrogen atom or together a double bond, $R^{15}$ represents a hydroxy group, or $R^{14}$ and $R^{15}$ together represent a [3,2c] pyrazole ring.

11. A compound according to claim 1, wherein
STEROID stands for a steroidal ring system of partial formula F, whereby $R^{11}$ represents a $C_{1-4}$-alkyl group or nitrile group.

12. A compound according to claim 1, which is
17aβ,4-Dihydroxy-D-homo-androstane-4,15-dien-3-one,
17aβ-Hydroxy-4-chloro-D-homo-androstane-4,15-dien-3-one,
17aβ-Hydroxy-4-bromo-D-homo-androstane-4,15-dien-3-one,
17aβ-Hydroxy-4-trifluoromethyl-D-homo-androstane-4,15-dien-3-one,
17aβ,11β-Dihydroxy-D-homo-androstane-4,15-dien-3-one,
17aβ,11β-Dihydroxy-D-homo-9α-fluoro-androstane-4,15-dien-3-one,
17aβ-Hydroxy-D-homo-androstane-1,4,15-trien-3-one,
17aβ-Hydroxy-D-homo-4-chloro-androstane-1,4,15-trien-3-one,
17aβ,4-Dihydroxy-D-homo-androstane-1,4,15-trien-3-one,
17aβ-Hydroxy-7α-methyl-D-homo-androstane-1,4,15-trien-3-one,
17aβ-Hydroxy-7α-methyl-4-chloro-D-homo-androstane-1,4,15-trien-3-one,
17aβ-Hydroxy-17α-methyl-androstane-4,15-dien-3-one,
17aβ-Hydroxy-17aα-trifluoromethyl-7α-methyl-androstane-4,15-dien-3-one,
17aβ,4-Dihydroxy-17aα-trifluoromethyl-androstane-4,15-dien-3-one,
17aβ-Hydroxy-17aα-trifluoromethyl-4-chloro-androstane-4,15-dien-3-one,
17aβ-Hydroxy-7α-methyl-D-homo-androstane-4,15-dien-3-one, 17aβ-Hydroxy-17α-pentafluoroethyl-androstane-4,15-dien-3-one,
17aβ-Hydroxy-D-homo-estra-4,15-dien-3-one,
17aβ,4-Dihydroxy-D-homo-estra-4,15-dien-3-one,
17aβ-Hydroxy-4-chloro-D-homo-estra-4,15-dien-3-one,
17aβ-Hydroxy-4-bromo-D-homo-estra-4,15-dien-3-one,
17aβ-Hydroxy-4-trifluoromethyl-D-homo-estra-4,15-dien-3-one,
17aβ-Hydroxy-17aα-methyl-D-homo-estra-4,15-dien-3-one,
17aβ-Hydroxy-17aα-methyl-4-chloro-D-homo-estra-4,15-dien-3-one,
17aβ-Hydroxy-17aα-trifluoromethyl-D-homo-estra-4,15-dien-3-one,
17aβ-Hydroxy-17aα-pentafluoroethyl-D-homo-estra-4,15-dien-3-one,
17aβ-Hydroxy-7α-methyl-D-homo-estra-4,15-dien-3-one,
17aβ-Hydroxy-7α-methyl-4-chloro-D-homo-estra-4,15-dien-3-one,
17aβ-Hydroxy-D-homo-estra-1,4,15-trien-3-one,
17aβ-Hydroxy-D-homo-4-chloro-estra-1,4,15-trien-3-one,
17aβ,4-Dihydroxy-D-homo-estra-1,4,15-trien-3-one,
17aα-Hydroxy-7α-methyl-D-homo-estra-1,4,15-trien-3-one,
17aβ-Hydroxy-7α-methyl-4-chloro-D-homo-estra-1,4,15-trien-3-one,
13-Ethyl-17aβ-hydroxy-D-homo-gona-4,15-dien-3-one,
13-Ethyl-17aβ-hydroxy-4-chloro-D-homo-gona-4,15-dien-3-one,
13-Ethyl-17aβ-hydroxy-7α-methyl-D-homo-gona-4,15-dien-3-one,
13-Ethyl-17aβ-hydroxy-17aα-methyl-D-homo-gona-4,15-dien-3-one,
13-Ethyl-17aβ-hydroxy-17aα-methyl-4-chloro-D-homo-gona-4,15-dien-3-one,
13-Ethyl-17aβ-hydroxy-D-homo-gona-1,4,15-trien-3-one,
13-Ethyl-17aβ-hydroxy-4-chloro-D-homo-gona-1,4,15-trien-3-one,
13-Ethyl-17aβ-hydroxy-7α-methyl-D-homo-gona-1,4,15-trien-3-one,
13-Ethyl-17aβ-hydroxy-7α-methyl-4-chloro-D-homo-gona-1,4,15-trien-3-one,
17aβ-Hydroxy-D-homo-5α-androst-15-en-3-one,
2-Oxa-17aβ-hydroxy-D-homo-5α-androst-15-en-3-one,
17aβ-Hydroxy-D-homo-5α-androstane-1,15-dien-3-one, or 2-Hydroxymethylene-17aβ-hydroxy-D-homo-5α-androst-15-en-3-one.

13. In a process for the production of a compound according to claim 1, of the formula I

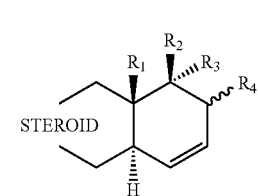

or a pharmaceutically acceptable salt thereof, the step wherein a compound of formula II

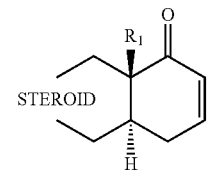

in which $R^1$ and STEROID have the meaning that is indicated in claim 1, is reacted in the presence of acids with acylating agents to form the dienol acetates and then reduced with reducing agents to the corresponding 17aβ-hydroxy-D-homo-$\Delta^{15}$-steroids.

14. A process according to claim 13, whereby:
compounds of formula II wherein STEROID has definition A are produced from Androst-4-ene-3,17-dione or dehydroepiandrosterone,
compounds of formula II wherein STEROID has definition B are produced from Estrone or 7α-methylestrone,
compounds of formula II wherein STEROID has definition C, D or E are produced from Epiandrosterone, and
compounds of formula II wherein STEROID has definition F are produced from 5α-Androst-2-en-17-one inturn produced from epiandrosterone.

15. A process according to claim 14, whereby functional groups that are contained in the starting materials above used to produce formula II are protected.

16. A process according to claim 15, whereby keto groups in the starting materials of partial structures A to F are protected as ketals or thioacetals.

17. A pharmaceutical composition comprising at least one compound according to claim 1.

18. A process for hormone replacement therapy in men or women, comprising administering a compound according to claim 1.

19. A process for birth control in men or women, comprising administering a compound according to claim 1.

20. A method for treating endometriosis, breast cancer or hypogonadism, comprising administering a compound according to claim 1.

21. A method for hormone replacement therapy, birth control, or treating endometriosis, breast cancer or hypogonadism, comprising administering 17aβ-Hydroxy-D-homo-androstane-4,15-dien-3-one.

* * * * *

UNITED STATES PATENT AND TRADEMARK OFFICE
CERTIFICATE OF CORRECTION

PATENT NO. : 7,388,003 B2
APPLICATION NO. : 10/923080
DATED : June 17, 2008
INVENTOR(S) : Ralf Wyrwa It is certified that error appears in the above-identified patent and that said Letters Patent is hereby corrected as shown below:

Column 13, line 65, reads "$R_3$" should read -- $R^3$ --

Column 15, line 61, reads "according to one of claim 1," should read -- according to claim 1, --

Column 16, line 1, reads "or a and $R^9$" should read -- or a methyl group --

Column 16, line 62, reads "...-17aαtrifluoromethyl-..." should read -- ...-17aα-trifluoromethyl-... --

Column 18, line 39, reads "inturn produced" should read -- in turn are produced --

Signed and Sealed this

Twenty-fourth Day of March, 2009

JOHN DOLL
*Acting Director of the United States Patent and Trademark Office*